US00PP32958P2

(12) United States Plant Patent
Van Swieten

(10) Patent No.: US PP32,958 P2
(45) Date of Patent: Apr. 6, 2021

(54) *PHALAENOPSIS* ORCHID PLANT NAMED 'PHALGRYLIA'

(50) Latin Name: ***Phalaenopsis* hybrid**
Varietal Denomination: PHALGRYLIA

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/998,092

(22) Filed: Aug. 20, 2020

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Nov. 4, 2020.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGRYLIA', particularly characterized by white flowers with a light purple shade and light purple-white lips, a moderately compressed petal shape, flower longevity on the plant of about 17 weeks, and is propagated by meristem tissue culture, is disclosed.

3 Drawing Sheets

Genus and species: *Phalaenopsis* hybrid.
Variety denomination: 'PHALGRYLIA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGRYLIA'.

The new *Phalaenopsis* plant is a product of a planned breeding program conducted by the inventor in Bleiswijk, the Netherlands. The objective of this breeding program was to create a new *Phalaenopsis* plant with attractive, white flowers with a light purple shade and light purple-white lips, suitable for potted plant production.

The new *Phalaenopsis* plant 'PHALGRYLIA' is a result of cross-pollination made by the inventor in September 2009 in Bleiswijk, the Netherlands, of the proprietary female, or seed parent, *Phalaenopsis* hybrid '01-3176' (unpatented) with the proprietary male, or pollen parent, *Phalaenopsis* hybrid '20421-08' (unpatented).

The new *Phalaenopsis* was selected by the inventor as a single plant within the progeny of the stated cross-pollination in a controlled greenhouse in Bleiswijk, the Netherlands, in September 2012. Asexual reproduction of the new *Phalaenopsis* plant by meristem tissue culture since 2013 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019 (Application no. 2019/0980), by Applicant who obtained the subject matter disclosed directly from the inventor. 'PHALGRYLIA' has not been made publicly available or sold anywhere in the world prior to the effective filing date of this application with the exception of sales or disclosures made one year or less before the effective filing date of this claimed invention by Applicant who obtained 'PHALGRYLIA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGRYLIA' as a new and distinct variety of *Phalaenopsis* plant:

1) White flowers with a light purple shade and light purple-white lips;
2) Petal shape is moderately compressed; and
3) Flower longevity on the plant is about 17 weeks.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2020. Colors in the photographs may differ from the color values cited in the detailed botanical description, which accurately describe the actual colors of the new variety.

DESCRIPTION OF THE NEW VARIETY

Figure 1:
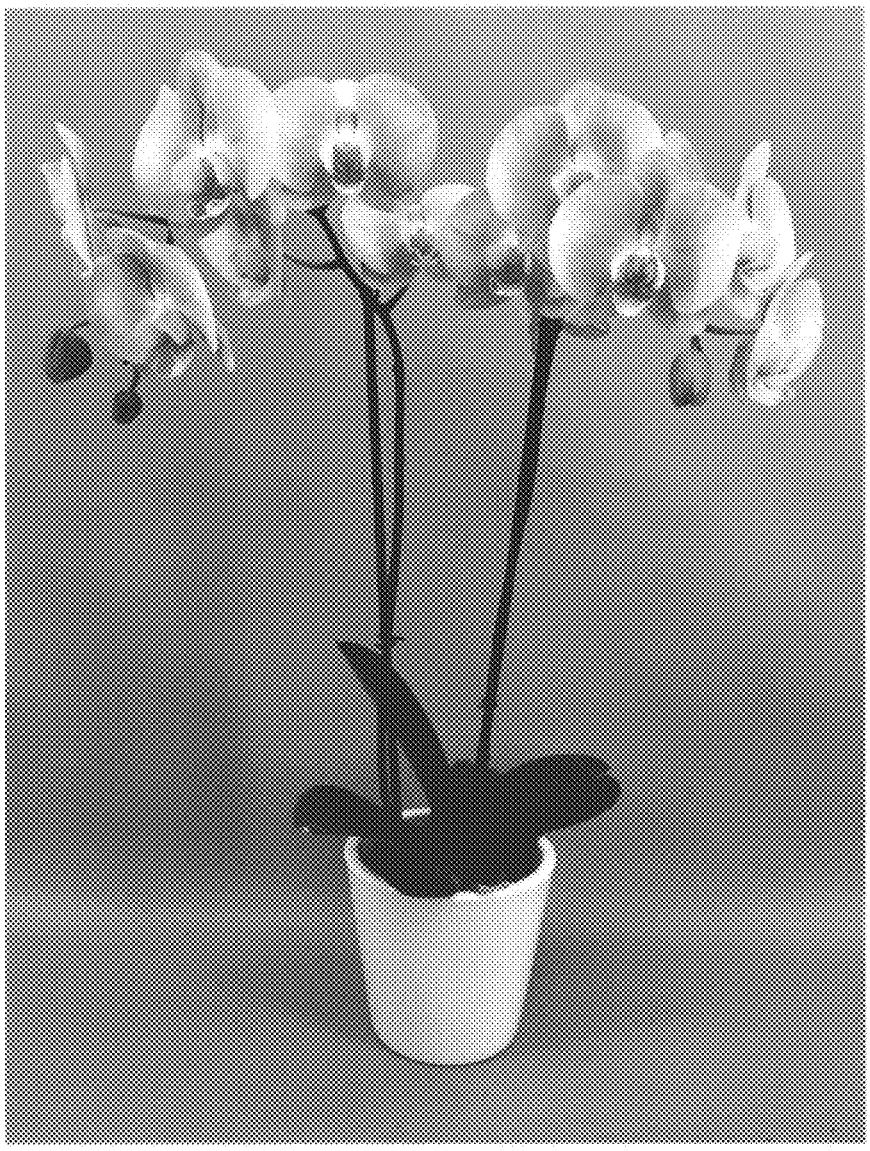
FIG. 1 shows the overall plant habit, including blooms, buds, and foliage of 'PHALGRYLIA'.
Figure 2:
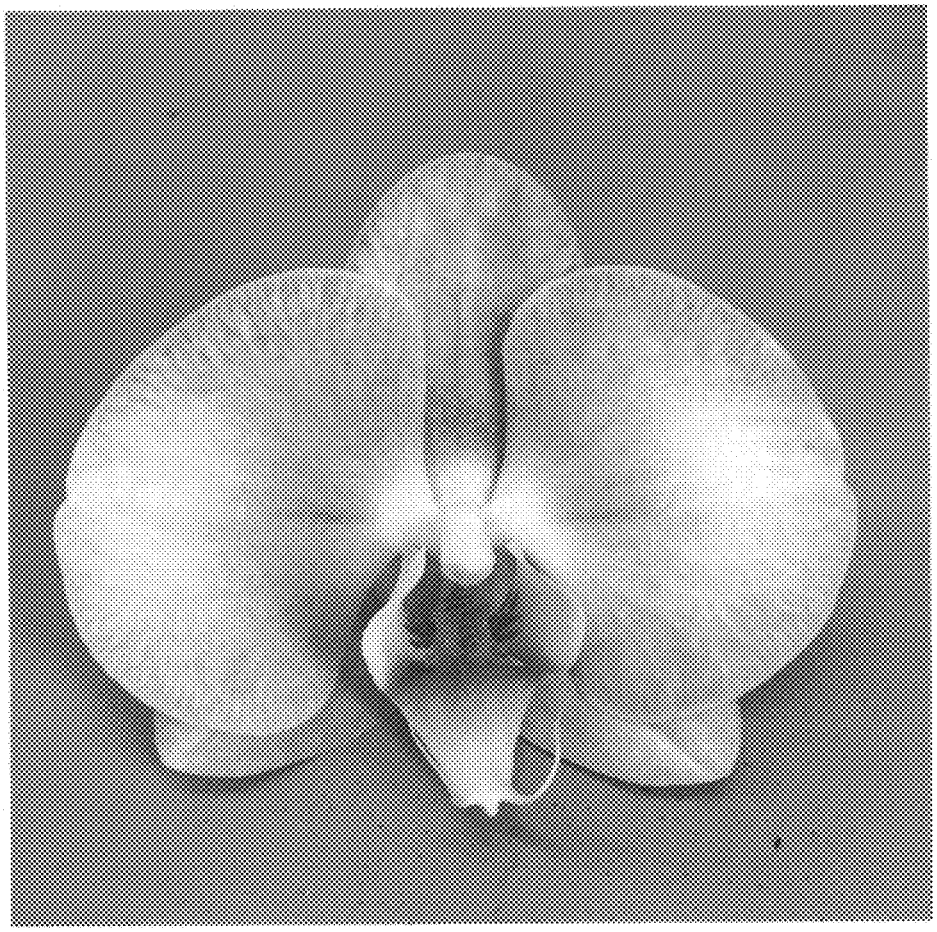
FIG. 2 shows a close-up of a flower of 'PHALGRYLIA'.
Figure 3:
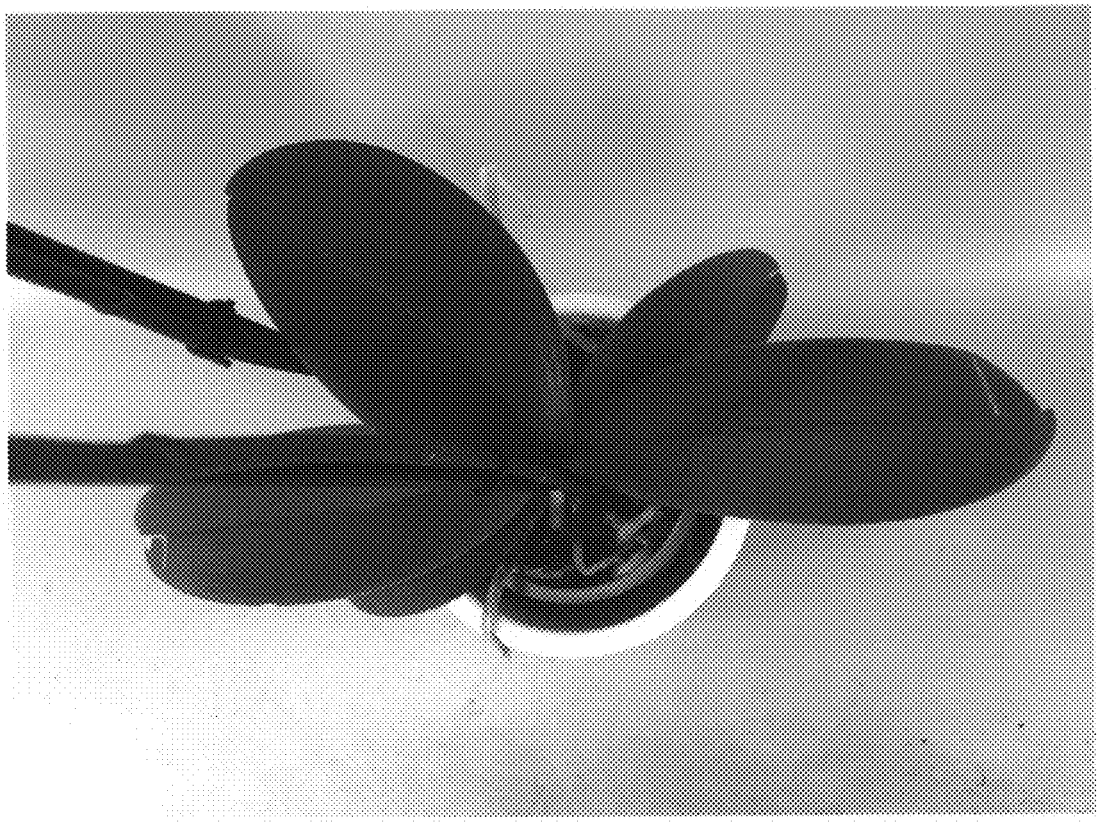
FIG. 3 shows an overhead view of the leaves of 'PHALGRYLIA'.

The following detailed description sets forth the distinctive characteristics of 'PHALGRYLIA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGRYLIA'.

Parentage:

*Female parent*.—*Phalaenopsis* cultivar '01-3176' (unpatented).

*Male parent*.—*Phalaenopsis* cultivar '20421-08' (unpatented).

Propagation:

*Type*.—Meristem tissue culture.

Roots:

*Root description*.—Greyed-green (something between RHS 190B and 190C) colored roots with branching lateral roots having small yellowish-green (RHS N144A) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 56.0 cm to 61.0 cm.

*Width* (*measured from leaf tips*).—About 32.0 cm to 34.0 cm.

*Vigor*.—Strong.

Leaves:

*Mature leaves*.—Quantity per plant: 6 to 7 leaves are produced before flowering. Length (fully expanded): 15.0 cm to 18.0 cm. Width: 7.0 cm to 9.0 cm. Position of the broadest part of the leaf: At the middle. Shape: Oblong. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 146A with a hint of brown (RHS 200C) margin toward the tip. Lower surface: RHS 146B with a hint of reddish-brown margin (RHS 200B) toward the tip. Texture (both upper and lower surfaces): Smooth. Thickness: 2.5 mm to 2.8 mm. Variegation: Absent. Venation: Pattern: Parallel. Color of the midvein: Upper surface: Green (RHS 146A). Lower surface: Yellow-green (RHS 146B) at the base and brown (RHS 200C) toward the tip.

Peduncle:

*Quantity per plant*.—1 to 2.

*Number of flowers per peduncle*.—8 to 13.

*Length*.—56.0 cm to 61.0 cm.

*Diameter*.—5.0 mm to 6.0 mm.

*Strength*.—Strong.

*Aspect*.—Upright to slightly pendent.

*Texture*.—Smooth.

*Color*.—Mix of reddish-brown (RHS 200B) and yellow-green (RHS 146C).

*Internode length*.—3.0 cm to 4.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 210.0 mm to 250.0 mm.

*Flowering time*.—First flowers can be expected 10 to 11 months after planting in a 12-cm pot.

*Flower*.—Height: 78.0 mm to 83.0 mm. Diameter: 95.0 mm to 100.0 mm. Depth of lip: 26.0 mm to 28.0 mm.

*Flower longevity*.—On the plant: 16 to 18 weeks.

*Flower shape*.—Flat.

*Fragrance*.—Absent.

*Flower bud*.—Average size: Medium to large. Length: 23.0 mm to 25.0 mm. Width: 19.0 mm to 21.0 mm. Shape: Egg shaped. Color: Touch of yellow-green (RHS N144C) at the base; mix of diluting red-purple (something in between RHS N77B and N79C) and light yellow-green (RHS 145C) toward the tip.

*Petals*.—Arrangement: Open/free. Shape: Semi-circular. Apex: Emarginated asymmetric. Margin: Weakly undulated. Length (from base to tip): 43.0 mm to 45.0 mm. Width: 59.0 mm to 61.0 mm. Position of the broadest part of the petal: Toward the base. Color (when fully opened): Upper surface: Basic color: White (RHS NN155C). Over color: Light purple shade (RHS 76A). Lower surface: Basic color: Very light purple (RHS 76D). Over color: Light purple shade (RHS 76A). Number of spots and stripes on the petals (upper surface): None. Color of spots and stripes on the petals (upper surface): Not applicable. Density of netting of the petals (upper surface): Low to medium. Color of the netting (upper surface): RHS 76A.

*Dorsal sepal*.—Shape: Elliptic. Apex: Obtuse to rounded symmetric. Margin: Entire. Length (from base to tip): 45.0 mm to 47.0 mm. Width: 33.0 mm to 35.0 mm. Position of the broadest part of the dorsal sepals: At the middle. Color (when fully opened): Upper surface: Basic color: White (RHS NN155C). Over color: Light reddish-purple shade (RHS N78D). Lower surface: Basic color: Very light purple (RHS 76C). Over color: Light reddish-purple (something in between RHS 76A and N78D). Number of spots and stripes on the dorsal sepals (upper surface): None. Color of spots and stripes on the dorsal sepals (upper surface): Not applicable. Density of netting of the dorsal sepals (upper surface): Low. Color of the netting: RHS 76A.

*Lateral sepals*.—Shape: Ovate. Apex: Obtuse asymmetric. Margin: Entire. Length (from base to tip): 46.0 mm to 48.0 mm. Width: 28.0 mm to 30.0 mm. Position of the broadest part of the lateral sepals: Toward the base. Color (when fully opened): Upper surface: Basic color: Light purple (something in between RHS 76A and 76B). Over color: Hint of white (RHS NN155C) and light yellow-green (RHS 145C) at the base. Lower surface: Basic color: Light reddish-purple (RHS N78D). Over color: Light yellow-green (RHS 145D) at the base; purplish-pink midvein (RHS N78C) toward the tip. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 14.0 mm to 16.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 22.0 mm to 23.0 mm. Width: 16.0 mm to 18.0 mm. Color: Upper surface: White (RHS NN155C) and hint of yellow (RHS 153D) at the margin on one side; touch of very light purple (RHS 76B) at the margin. Lower surface: White (RHS NN155C); touch of greenish-yellow (something in between RHS 153C and 153D) at the margin on one side; hint of light purple (RHS 76A) toward whiskers. Number of spots and stripes on the lateral lobe: Few stripes at the base. Color of spots and stripes on the lateral lobe: RHS 184B. Density of netting of the lateral lobe: None. Color of the netting: None.

*Apical lobe*.—Shape: Triangular. Margin: Entire. Length: 21.0 mm to 23.0 mm. Width: 22.0 mm to 24.0 mm. Color: Upper surface: Light purple (RHS 76A) with a touch of greenish-yellow (RHS 153B) at the base; greenish-yellow wings (RHS 153B) and white (RHS NN155C) toward whiskers. Lower surface: Light reddish-purple (RHS N78D); greenish-yellow wings (RHS 153C); white (RHS NN155C) with a hint of very light purple (RHS 76B) toward whiskers. Number of spots and stripes on the apical lobe: None. Color of spots and stripes on the apical lobe: Not applicable. Density of netting of the apical lobe: None. Color of the netting: None.

*Callus*.—Average size: Medium. Height: 7.0 mm to 8.0 mm. Length: 6.0 mm to 7.0 mm. Width: 4.0 mm to 5.0 mm. Color: Yellow (RHS 8A); dotted (RHS 175A).

Reproductive organs:

*Column*.—Length: 7.0 mm to 8.0 mm. Diameter: 5.0 mm to 6.0 mm. Color: White (RHS NN155C) (some of flowers with a small, very light purple region (RHS 76B) at the middle on the upper side).

*Pollinia*.—Quantity: 2. Diameter: 0.9 mm to 1.1 mm. Color: Orange-yellow (RHS 23A).

*Ovary*.—Length: 14.0 mm to 16.0 mm. Diameter: 2.4 mm to 2.7 mm.

*Pedicel*.—Length: 48.0 mm to 50.0 mm. Diameter: 2.8 mm to 3.2 mm. Texture: Smooth. Color: Hint of dark red (something in between RHS 187A and 187B) at the base; light yellow-green (RHS 145C) and very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGRYLIA' differs from female parent plant '01-3176' (unpatented) in that 'PHALGRYLIA' has flowers with a shaded pattern and a medium curvature of the lateral lobe, whereas '01-3176' has flowers with a flecked pattern and a strong curvature of the lateral lobe.

'PHALGRYLIA' differs from male parent plant '20421-08' (unpatented) in that 'PHALGRYLIA' has columns that are white, with some flowers having a small, very light purple region at the middle on the upper side, whereas '20421-08' has columns that are very light purple. Additionally, 'PHALGRYLIA' has smaller flowers than '20421-08'.

'PHALGRYLIA' is most similar to the commercial *Phalaenopsis* plants named 'PHALGAQXYK' (U.S. Plant Pat. No. 30,872) and 'PHALGAKXYN' (U.S. Plant patent application Ser. No. 16/602,631). 'PHALGRYLIA' differs from the commercial variety 'PHALGAQXYK' in that 'PHALGRYLIA' has columns that are white, with some flowers having a small, very light purple region at the middle on the upper side, whereas 'PHALGAQXYK' has columns that are very light purple at the base with a purplish-pink region toward the tip. Additionally, 'PHALGRYLIA' has shorter leaves and larger flowers than 'PHALGAQXYK'.

'PHALGRYLIA' differs from the commercial variety 'PHALGAKXYN' in that 'PHALGRYLIA' has columns that are white, with some flowers having a small, very light purple region at the middle on the upper side and lateral sepals with an overcolor that is slightly light yellow-green with purplish-red dots at the base, whereas 'PHALGAKXYN' has columns that are very light purple and laterals sepals with an overcolor that is light reddish-purple at the base and very light purple blush.

I claim:

1. A new and distinct variety of *Phalaenopsis* plant named 'PHALGRYLIA', substantially as described and illustrated herein.

* * * * *